United States Patent [19]
McConnell

[11] Patent Number: 5,280,342
[45] Date of Patent: Jan. 18, 1994

[54] OPTICAL GRID PROJECTION SYSTEM FOR SURGICAL APPLICATIONS

[76] Inventor: Timothy P. McConnell, 1431 Cherokee Trail #46, Knoxville, Tenn. 37920

[21] Appl. No.: 930,366

[22] Filed: Aug. 17, 1992

[51] Int. Cl.$^5$ .............................................. G01B 11/24
[52] U.S. Cl. ................................ 356/376; 250/237 G
[58] Field of Search ................... 356/2, 376, 374, 375, 356/121, 122, 243; 354/77, 290, 62, 65, 77, 78; 250/237 G; 353/28, 30, 40, 41, 94

[56] References Cited

U.S. PATENT DOCUMENTS

| | | | |
|---|---|---|---|
| 4,070,683 | 1/1978 | Altschuler et al. | 356/2 |
| 4,564,295 | 1/1986 | Halioua | 356/376 |
| 4,575,805 | 3/1986 | Moermann et al. | 356/376 |
| 4,657,394 | 4/1987 | Halioua | 356/376 |
| 4,802,759 | 2/1989 | Matsumoto et al. | 356/376 |
| 4,825,263 | 4/1989 | Desjardins et al. | 356/376 |
| 4,846,577 | 7/1989 | Grindon | 356/376 |
| 4,952,149 | 8/1990 | Duret et al. | 433/215 |
| 4,964,770 | 10/1990 | Steinbichler et al. | 433/223 |
| 4,965,442 | 10/1990 | Girod | 250/201.7 |
| 4,987,432 | 1/1991 | Landwehr | 354/77 |
| 5,027,281 | 6/1991 | Rekow et al. | 364/474.24 |

OTHER PUBLICATIONS

Timothy P. McConnell, "Facefinder", Abstract published in American Assoc. Oral and Maxillofacial Surgery, p. 61 on or about May 1, 1991.

Primary Examiner—Richard A. Rosenberger
Assistant Examiner—Hoa Q. Pham
Attorney, Agent, or Firm—Pitts & Brittian

[57] ABSTRACT

A profilometry system useful for surgeons dealing with malformation of body portions of patients. A collimated light beam is projected through one of a selected number of customized grid patterns so as to impress the selected grid pattern upon the body portion. The surgeon can determine from this impressed grid any deviation from certain "standard" orientation goals and thus what reconstruction is needed to correct for the malformation. The same system can then be used to ascertain the profile after any reconstruction procedures. In the preferred embodiment a slide projector system, with focusing, is utilized for providing the collimated light beam and selecting a desired grid pattern.

20 Claims, 3 Drawing Sheets

OPTICAL GRID PROJECTION SYSTEM FOR SURGICAL APPLICATIONS

TECHNICAL FIELD

The present invention relates to optical profilometry systems for determining the relationship between actual bone/tissue configuration and a preferred configuration of a patient, and more particularly to an optical profilometry system for projecting a selected grid array upon the patient for determining this relationship.

background art

Reconstructive surgery is commonly utilized to correct for cosmetic deformities. For example, the orientation, size and shape of a patient's nose is correctable by surgery. In addition, this type of surgery is frequently utilized for traumatic- and congenital-produced facial defects to restore bone structure to aesthetically pleasing orientation. Similarly, dental work is often utilized to provide symmetry of the teeth and reshape facial contours. While these examples of constructive surgery relate to the head, similar surgery is utilized to change other contours of the patient.

In any of these and similar types of surgery, it is desirable to achieve some preselected aesthetically pleasing shape, contour or orientation. This preselected characteristic can be that of the original configuration of the patient, but is more often that of a "standard" configuration. However, it is often difficult to completely achieve the desired configuration because during the surgery the surgeon has no guide but must work from memory. Furthermore, after healing has been achieved, the results must be evaluated as to success in achieving the desired configuration, e.g., symmetry as compared left to right.

Several optical profilometer systems are known for generating information as to head contours, in particular facial contours. Typical of such systems are those described and shown in U.S. Pat. Nos. 4,825,263 issued to P. J. Desjardins, et.al., on Apr. 25, 1989; 4,657,394 issued to M. Halioua on Apr. 14, 1987; 4,846,577 issued to J. R. Grindon on Jul. 11, 1989; 4,964,770 issued to H. Steinbichler, et.al., on Oct. 23, 1990; 4,952,149 issued to F. Duret, et.al., on Aug. 28, 1990; and 4,564,295 issued to M. Halioua on Jan. 14, 1986. Other references generally related to the subject of the present invention are U.S. Pat. Nos. 4,987,432 issued to U. M. Landwehr on Jan. 22, 1991; 4,965,442 issued to B. Girod, et.al., on Oct. 23, 1990; and 5,027,281 issued to E. D. Rekow, et.al., on Jun. 25, 1991. While all of these references solve some particular problem, they are not directed to a ready manner of determining profiles of objects as needed during maxillofacial surgery and related reconstruction areas. In particular, they are not adaptable to the several problems that exist in facial, dental and related profiles to achieve desired aesthetic goals.

Accordingly, it is an object of the present invention to provide a system for projecting a selectable grid pattern upon an object whereby the contour of the object can be visually related to the projected grid pattern.

It is another object of the present invention to provide a system for directing a collimated light beam through a grid of a selected configuration so as to impinge an optical grid upon an object under investigation for contours and locations of components.

Another object of the present invention is to provide a series of customized grid patterns for projection upon an object under investigation, each of the grid patterns selected to provide desired information as to orientation of specific features of the object.

A further object of the present invention is to provide an optical profilometry system useful in reconstructive surgical procedures, particularly of the head of a patient, to determine symmetry, shape, size and other aspects of facial features.

These and other objects of the present invention will become apparent upon a consideration of the drawings referred to hereinafter together with a complete description thereof.

DISCLOSURE OF THE INVENTION

In accordance with the present invention, there is provided an optical profilometry system utilizing a collimated light beam and a group of selected customized grid pattern transparencies for interposing into the light beam to project upon a given object a optical grid pattern of the selected grid configuration. Each of the grid patterns has reference lines whereby shape, size, symmetry, overall profile and similar characteristics of features of the object can be determined. In the preferred embodiment, there can be an adjustable lens for centering the grid pattern relative to the patient. Also, this preferred embodiment can have a moveable element of the grid pattern for assistance in orienting the symmetry potential of the pattern, and reference patterns can be added to assist in focus and proper directional orientation.

BEST MODE FOR CARRYING OUT THE INVENTION

Figure 1:
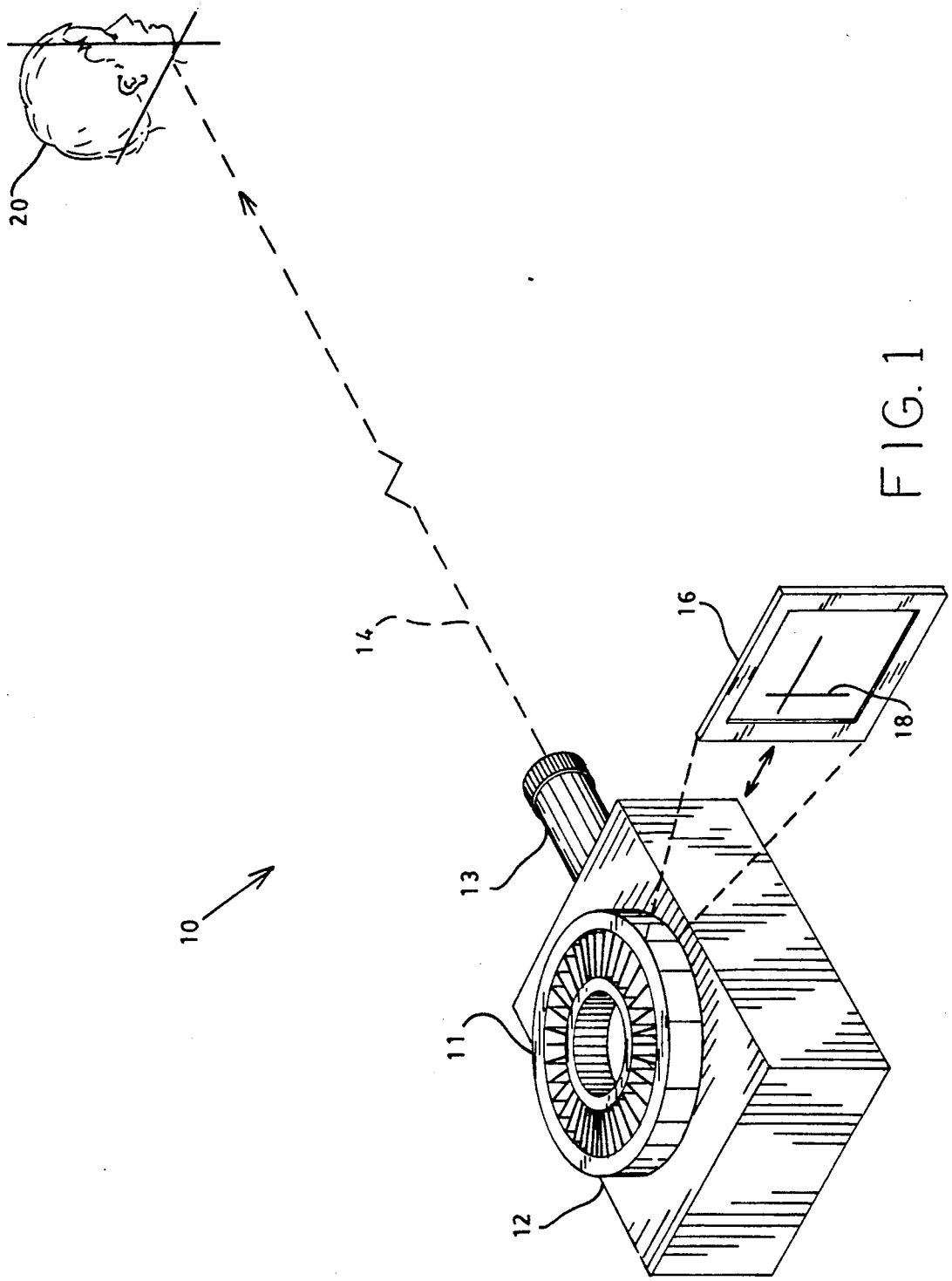
FIG. 1 is a schematic block diagram of the components of the present invention

A schematic drawing of the system 10 of the present invention is shown in FIG. 1. A light source 12 generates a collimated light beam 14 for impacting and passing through a selected transparency/slide 16. This transparency/slide carries a customized grid pattern 18, with the particular selectable patterns described in more detail hereinafter. The resultant projected grid pattern then impinges upon a subject, in this case a patient's head 20. It will be recognized that a suitable means for creating the collimated light beam and impinging it upon the transparency is a conventional slide projector changer 11 with a focusing lens 13. In this manner, a selected one of many slides carrying customized grid patterns can be chosen for a particular application.

Figure 2A:
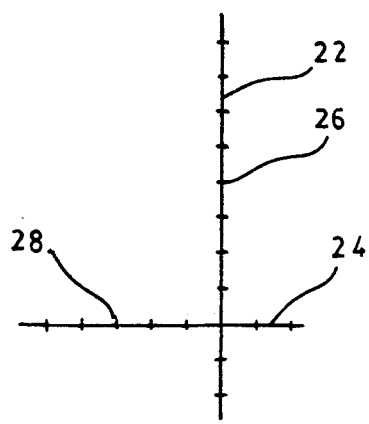
FIGS. 2A through 2D is a drawing illustrating a number of selectable customized grid patterns that are useful with the present invention. These can be made as either "negatives" or "positives" of the grid pattern in the form of transparencies or slides.
Figure 2B:
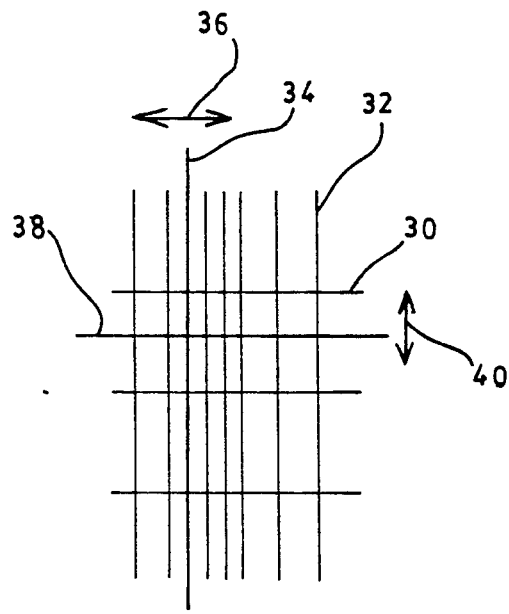

Numerous customized grid patterns that will be of help in evaluating profiles and features of objects are shown in portions of FIGS. 2A-2D. For example, FIG. 2A is a grid pattern for determining profiles related to a single vertical line 22 and a single horizontal line 24. Although illustrated as not being symmetrical, the lines 22, 24 can be symmetrically arranged into a uniform cross configuration. This figure includes an optional use of "hash" marks 26, 28 on the lines 22, 24, respectively. Similar marks can be applied to other of the grid patterns. FIG. 2B provides a grid of crossing parallel lines, where the horizontal parallel lines 30 are equally spaced and the vertical parallel lines 32 have varying spacing that are symmetrically arranged with regard to a center line. Shown in this figure is another option of all of the grid patterns. This option is the provision of a moveable vertical line 34 that can be moved as indicated by the double-ended arrow 36, and a moveable horizontal line 38 that can be moved as indicated by the double-ended arrow 40. These lines, which can be created at the optical focus of the projection means, can be used to as "pointer" lines to orient a special feature of the object upon which the grid pattern is being projected.

Figure 2C:
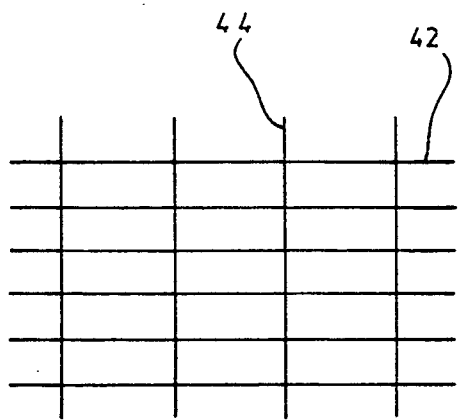

FIG. 2C depicts another typical grid pattern in the form of equally spaced parallel horizontal 42 and vertical lines 44 where one or the other has a different spacing distance than the other. This figure, as well as FIGS. 2B and 2D, illustrate the relative relationships for a well recognized preferred aesthetic appearance; namely, a ratio of 1:1.66 (e.g., 3:5).

Figure 2D:
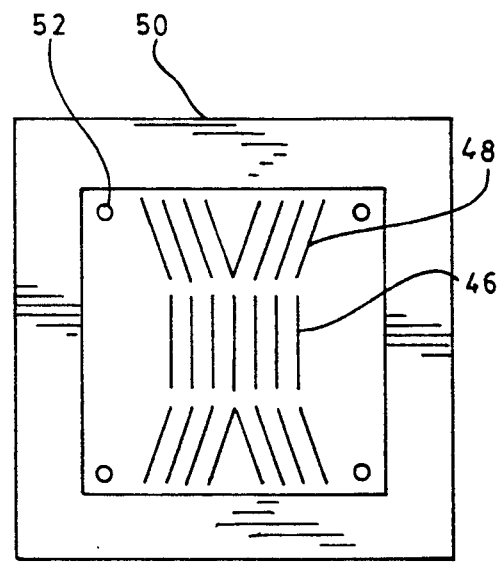

FIG. 2D illustrates a combination of parallel and equally-spaced vertical lines 46 together with equally-spaced lines 48 at an angle to the vertical. Of course, it will be understood that other combinations of straight lines, together with lines having a given angle or curvature, can be combined to produce a grid for a selected application. This FIG. 2D illustrates the use of a grid pattern mounted in a slide mount 50. In addition, another option of the present invention, that is useful for any of the grid patterns, is a series of small circles 52 in the corners (or other locations near the edge). It will be recognized that if the image of these circles upon an object are all in focus, the light beam (and the grid pattern) are being projected at an angle normal to the plane of the object; however, if some are not in focus, the light beam is not properly aimed.

Figure 3:
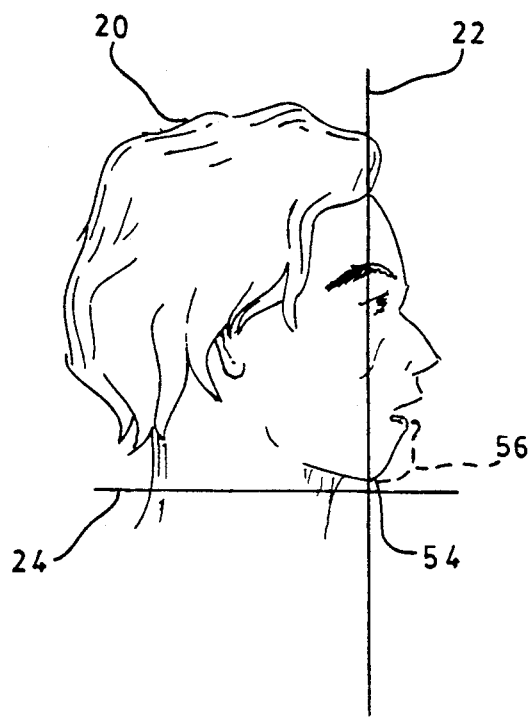
FIG. 3 is a drawing illustrating the use of a selected grid pattern to determine deviation of an individual's facial profile from standard profile.

A grid pattern like that of FIG. 2A is utilized, for example, to ascertain alignment of facial portions. A typical profilometry of this type is illustrated in FIG. 3. In this instance, a patient 20 has a greatly receding chin 54 as compared to a more normal chin indicated with a dashed line 56. After an profilometry analysis of this type where distances can be measured related to deviation from "standard", a reconstruction of the facial bones, and perhaps the teeth, can be undertaken to correct the profile to the desired contours.

Figure 4:
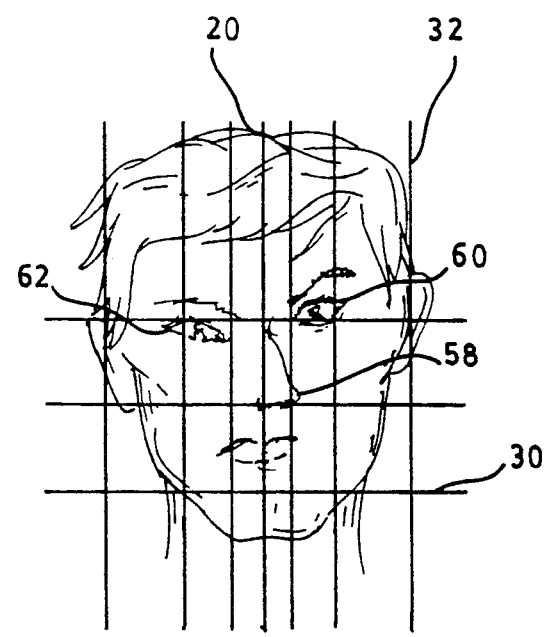
FIG. 4 is a drawing illustrating the use of a selected grid pattern to determine deviation in symmetry of a frontal view of a patient from a standard orientation.

A frontal profilometry analysis is depicted in FIG. 4 utilizing the grid pattern of FIG. 2B. In this example, the nose 58 of the patient is oriented angularly to the center vertical line of the grid. Further, the left eye 60 is shown as being higher than the right eye 62 (either can be at non-normal positions). Likewise, the non-alignment of the patient's ears 48, 50 are depicted. With this analysis, a determination can be made as to the most appropriate of reconstruction options that can be made to achieve proper symmetry of the facial units.

It will be recognized that while FIG. 3 and FIG. 4 illustrate a patient's head, other body parts can be analyzed in a similar manner to determine any desirable correction of position and size. Such portions could be, for example, shoulder location, back curvature, etc. In any of the applications, the system is used with customized grid patterns to analyze problems, and then to evaluate desired position, orientation, etc. after any reconstruction has been accomplished.

From the foregoing it will be understood by persons skilled in the art that a system has been described and shown that will be of value to surgeons of all types. It will permit an evaluation of orientation/position problems of a patient, and then the success of the reconstruction procedures. The same principle can be used for projection against an x-ray for the purpose of determining any desired changes.

While certain customized grid patterns have been illustrated, this is for the purpose of generally describing the present invention and not for the purpose of limiting the same. The invention is to be limited only by the appended claims and their equivalents.

I claim:

1. A profilometry system for determining the relationship between actual bone/tissue configuration of a selected portion of a patient with a preferred configuration, said system comprising:
   a grid pattern member having a selected customized grid design defining by substantially transparent areas and substantially non-transparent areas;
   a source of a light beam for being directed through said grid pattern member to produce a replica of said grid design upon a selected portion of a patient whereby a relationship of bone/tissue of the patient is visually observed relative to said grid design;
   a changer means for selectively interchanging said grid pattern member with other grid pattern members having other customized grid designs; and
   a focusing means for focusing said replica of said grid design upon the selected portion of the patient.

2. The profilometry system of claim 1 wherein said grid pattern member has said customized grid design defined by at least one vertical line and one horizontal line.

3. A profilometry system of claim 2 wherein said customized grid design includes equally-spaced calibration marks along said at least one vertical line and along said at least one horizontal line.

4. The profilometry system of claim 1 wherein said grid pattern member has said customized grid design defined by a plurality of equally spaced vertical lines and a plurality of equally spaced horizontal lines.

5. The profilometry system of claim 1 wherein said grid pattern member has said customized grid design defined by a plurality of vertical lines spaced symmetrically from a center point and a plurality of equally spaced horizontal lines.

6. The profilometry system of claim 1 wherein said grid pattern member has said customized grid design defined by a first plurality of parallel straight lines and a second plurality of straight lines oriented at an acute angle to aid first plurality of lines.

7. The profilometry system of claim 1 further comprising means associated with said focusing means for including a moveable vertical line and a moveable horizontal line in said grid design whereby said moveable vertical line and said moveable horizontal are used as pointer lines to identify a particular point on said replica of said grid design on the body portion of the patient.

8. The profilometry system of claim 1 wherein said grid pattern member includes pattern portions for visually identifying conformance of said replica pattern to uniform focus occurring when said light beam is normal to the body portion of the patient.

9. The profilometry system of claim 1 wherein said grid design has a width height dimensional relationship of about 1:1.66.

10. The profilometry system of claim 1 wherein said grid pattern member is held in a slide mount, and said changer means is a slide changer.

11. A profilometry system for determining the relationship between actual bone/tissue configuration of a selected portion of a patient with a preferred configuration, said system comprising:
- a grid pattern member having a selected customized grid design defined by substantially transparent areas and substantialy non-transparent areas, said grid pattern member held in a slide mount;
- a source of a light beam for being directed through said grid pattern member to produce a replica of said grid design upon a selected portion of a patient whereby said relationship of bone/tissue of the patient is visually observed relative to said grid design;
- focusing means for focusing said replica of said grid design upon the selected portion of the patient; and
- a slide changer for interchanging said grid pattern member with another selected grid pattern member.

12. The profilometry system of claim 11 wherein said grid pattern member has said customized grid design defined by at least one vertical line and one horizontal line.

13. The profilometry system of claim 11 further comprising means associated with said focusing means for including a moveable vertical line and a moveable horizontal line in said grid design whereby said moveable vertical line and said moveable horizontal line are used as pointer lines to identify a particular point on said replica of said grid design on the body portion of the patient.

14. The profilometry system of claim 11 wherein said grid pattern member has said customized grid design defined by a plurality of equally spaced vertical lines and a plurality of equally spaced horizontal lines.

15. The profilometry system of claim 11 wherein said grid pattern member has said customized grid design defined by a plurality of vertical lines spaced symmetrically from a center point and a plurality of equally spaced horizontal lines.

16. The profilometry system of claim 11 wherein said grid pattern member has said customized grid design defined by a first plurality of parallel straight lines and a second plurality of straight lines oriented at an acute angle to said first plurality of lines.

17. The profilometry system of claim 11 wherein said grid pattern member includes pattern portions for visually identifying conformance of said replica pattern to uniform focus occurring when said light beam is normal to the body portion of the patient.

18. The profilometry system of claim 11 wherein said grid design has a width/height dimensional relationship of about 1:1.66.

19. A profilometry system for determining the relationship between actual bone/tissue configuration of a selected portion of a patient with a preferred configuration, said system comprising:
- a grid pattern member having a selected customized grid design defined by substantially transparent areas and substantially non-transparent areas, said grid design having a width-to-height dimensional ratio of about 1:1.66; and
- a source of a collimated light beam for being directed through said grid pattern member to produce a replica of said grid design upon a selected portion of a patient whereby a relationship of bone/tissue of the patient is visually observed relative to said grid design.

20. The profilometry system of claim 19 wherein said grid pattern member has said customized grid design defined by at least one vertical line and one horizontal line.

* * * * *